United States Patent
Leibowitz et al.

(10) Patent No.: US 11,849,924 B2
(45) Date of Patent: Dec. 26, 2023

(54) TISSUE RESECTING INSTRUMENTS INCLUDING TISSUE COLLECTION CARTRIDGES

(71) Applicant: Covidien LP, Mansfield, MA (US)

(72) Inventors: Dalia P. Leibowitz, Cambridge, MA (US); Dale E. Whipple, Nashua, NH (US); Timothy J. Wood, Wilmington, MA (US)

(73) Assignee: Covidien LP, Mansfield, MA (US)

( * ) Notice: Subject to any disclaimer, the term of this patent is extended or adjusted under 35 U.S.C. 154(b) by 585 days.

(21) Appl. No.: 16/891,758

(22) Filed: Jun. 3, 2020

(65) Prior Publication Data

US 2020/0405274 A1 Dec. 31, 2020

Related U.S. Application Data

(60) Provisional application No. 62/867,285, filed on Jun. 27, 2019.

(51) Int. Cl.
| | |
|---|---|
| *A61B 10/00* | (2006.01) |
| *A61B 17/3207* | (2006.01) |
| *G01N 1/28* | (2006.01) |
| *G01N 1/31* | (2006.01) |
| *A61B 17/32* | (2006.01) |
| *A61B 17/00* | (2006.01) |
| *A61B 90/00* | (2016.01) |
| *A61B 10/02* | (2006.01) |
| *A61B 17/22* | (2006.01) |

(52) U.S. Cl.
CPC .. *A61B 10/0096* (2013.01); *A61B 17/320783* (2013.01); *G01N 1/286* (2013.01);
(Continued)

(58) Field of Classification Search
CPC ........ A61B 10/0096; A61B 17/320783; A61B 10/0275; A61B 2017/00115; A61B 2017/00367; A61B 2017/0042; A61B 2017/22079; A61B 2017/320064; A61B 2090/0807; A61B 2017/320028;
(Continued)

(56) References Cited

U.S. PATENT DOCUMENTS

| | | |
|---|---|---|
| 5,403,276 A | 4/1995 | Schechter et al. |
| 5,782,795 A | 7/1998 | Bays |

(Continued)

FOREIGN PATENT DOCUMENTS

| | | | | |
|---|---|---|---|---|
| WO | WO-2017016676 A1 | * | 2/2017 | ......... A61B 10/0096 |

*Primary Examiner* — Richard G Louis

(74) *Attorney, Agent, or Firm* — Carter, DeLuca & Farrell LLP

(57) ABSTRACT

A tissue resecting instrument includes a drive assembly coupled to an inner cutting shaft and configured to drive translation and/or rotation of the inner cutting shaft, a trigger coupled to the drive assembly and configured for manual actuation to drive the drive assembly, a vacuum generator configured to generate vacuum to suction cut tissue through the inner cutting shaft and into the vacuum generator, and a tissue collection cartridge configured to engage the housing. The tissue collection cartridge defines a port configured to communicate with the vacuum generator such that the vacuum generator urges cut tissue from the vacuum generator through the port into the tissue collection cartridge. The tissue collection cartridge may include at least one histological agent disposed therein, may include a fill indicator configured to indicate a fill level of tissue within the tissue collection cartridge, and/or may include a latch configured to seal the port closed.

12 Claims, 6 Drawing Sheets

(52) U.S. Cl.
CPC ............ *G01N 1/31* (2013.01); *A61B 10/0275* (2013.01); *A61B 2017/0042* (2013.01); *A61B 2017/00115* (2013.01); *A61B 2017/00367* (2013.01); *A61B 2017/22079* (2013.01); *A61B 2017/320064* (2013.01); *A61B 2090/0807* (2016.02); *G01N 2001/2873* (2013.01)

(58) Field of Classification Search
CPC .... A61B 2017/32004; A61B 2217/005; A61B 17/32002; G01N 1/286; G01N 1/31; G01N 2001/2873
See application file for complete search history.

(56) References Cited

U.S. PATENT DOCUMENTS

| | | | |
|---|---|---|---|
| 8,012,153 B2 | 9/2011 | Woloszko et al. | |
| 8,986,334 B2 | 3/2015 | Mark et al. | |
| 9,060,760 B2 | 6/2015 | Sullivan et al. | |
| 9,107,691 B2 | 8/2015 | Fojtik | |
| 9,486,233 B2 | 11/2016 | Bek et al. | |
| 9,913,629 B1 | 3/2018 | Sullivan et al. | |
| 10,022,140 B2 | 7/2018 | Germain et al. | |
| 2005/0209622 A1 | 9/2005 | Carrison | |
| 2007/0213755 A1 | 9/2007 | Beckman et al. | |
| 2009/0270895 A1 | 10/2009 | Churchill et al. | |
| 2010/0152611 A1* | 6/2010 | Parihar | A61B 10/0275 600/566 |
| 2010/0312140 A1* | 12/2010 | Smith | A61B 10/0275 600/566 |
| 2013/0172870 A1 | 7/2013 | Germain et al. | |
| 2013/0211321 A1 | 8/2013 | Dubois et al. | |
| 2015/0305765 A1 | 10/2015 | Fojtik et al. | |
| 2017/0049441 A1 | 2/2017 | Sauer et al. | |
| 2017/0105607 A1 | 4/2017 | Truckai | |
| 2017/0105736 A1 | 4/2017 | Chen et al. | |
| 2017/0333119 A1 | 11/2017 | Truckai | |
| 2018/0098755 A1* | 4/2018 | Keller | A61B 10/0096 |

* cited by examiner

TISSUE RESECTING INSTRUMENTS INCLUDING TISSUE COLLECTION CARTRIDGES

CROSS REFERENCE TO RELATED APPLICATIONS

This application claims the benefit of U.S. Provisional Application Ser. No. 62/867,285, filed Jun. 27, 2019, the entire contents of which are incorporated by reference herein.

FIELD

The present disclosure relates generally to the field of tissue resection. In particular, the present disclosure relates to tissue resecting instruments including tissue collection cartridges.

BACKGROUND

Tissue resecting instruments are commonly used in endoscopic tissue resection procedures within an organ, such as a uterus, by inserting an endoscope (or hysteroscope) into the uterus and passing the tissue resection instrument through the endoscope (or hysteroscope) and into the uterus. With respect to such endoscopic tissue resection procedures, tissue is resected at the surgical site and suctioned proximally through the tissue resecting instrument, along with fluid at the surgical site.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue resecting instrument including a housing, an outer shaft, an inner cutting shaft, a drive assembly, a trigger, a vacuum generator, and a tissue collection cartridge. The outer shaft extends distally from the housing and defines a window at a distal end portion thereof. The inner cutting shaft extends through the outer shaft and is configured to translate and/or rotate relative to the outer shaft to cut tissue extending through the window. The drive assembly is coupled to the inner cutting shaft and configured to drive the translation and/or rotation of the inner cutting shaft. The trigger is coupled to the drive assembly such that manual actuation of the trigger actuates the drive assembly to drive the translation and/or rotation of the inner cutting shaft. The vacuum generator is coupled to the drive assembly and the inner cutting shaft such that, during a first portion of the actuation of the drive assembly, the vacuum generator is configured to generate vacuum to suction cut tissue through the inner cutting shaft and into the vacuum generator. The tissue collection cartridge is configured to releasably engage the housing and defines a port configured to communicate with the vacuum generator such that, during a second portion of the actuation of the drive assembly, the vacuum generator urges cut tissue from the vacuum generator through the port into the tissue collection cartridge.

In aspects of the present disclosure, the trigger is pivotably coupled to the housing and movable relative thereto between an un-actuated position and an actuated position to drive the drive assembly to translate the inner cutting shaft between a more-proximal position and a more-distal position. In such aspects, the first portion of the actuation of the drive assembly may correspond to movement of the trigger from the un-actuated position to the actuated position. Additionally or alternatively, the second portion of the actuation of the drive assembly may correspond to movement of the trigger from the actuated position to the un-actuated position.

In aspects of the present disclosure, the tissue collection cartridge includes a latch operably associated with the port and configured such that, upon disengagement of the tissue collection cartridge from the housing, the latch seals the port closed.

In aspects of the present disclosure, the latch includes first and second latch arms configured to move from a disengaged position to an engaged position to seal the port closed.

In aspects of the present disclosure, the tissue collection cartridge further includes an internal filter and a drain port. The internal filter is configured to retain tissue therein and permit passage of fluid therethrough to drain out through the drain port. In such aspects, a second latch operably associated with the drain port may be provided. The second latch is configured, upon disengagement of outflow tubing from the drain port, to seal the drain port closed.

In aspects of the present disclosure, the tissue collection cartridge includes a fill indicator configured to provide an indication to a user as to a fill level of tissue within the tissue collection cartridge.

In aspects of the present disclosure, the fill indicator is a mechanical flag. The mechanical flag, in aspects, is coupled to a spring-biased wall disposed within the tissue collection cartridge such that, as tissue fills the tissue collection cartridge, tissue moves the spring-biased wall to thereby move the mechanical flag.

In aspects of the present disclosure, the fill indicator is a sensory output device configured to output an audible and/or visual indicator. The sensory output device, in aspects, is coupled to at least one switch disposed within the tissue collection cartridge such that, as tissue fills the tissue collection cartridge, the at least one switch is actuated, thereby triggering the output of the sensory output device.

In aspects of the present disclosure, the tissue collection cartridge includes at least one histological agent disposed therein. The at least one histological agent may include a staining agent, a clearing agent, a fixing agent, a dehydration agent, and/or an infiltration agent.

In aspects of the present disclosure, the at least one histological agent is disposed within a capsule. The capsule may be a fluid-soluble capsule, a time-release capsule, or a frangible capsule.

In aspects of the present disclosure, the tissue collection chamber includes an activator plunger configured to selectively penetrate the capsule to release the at least one histological agent.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
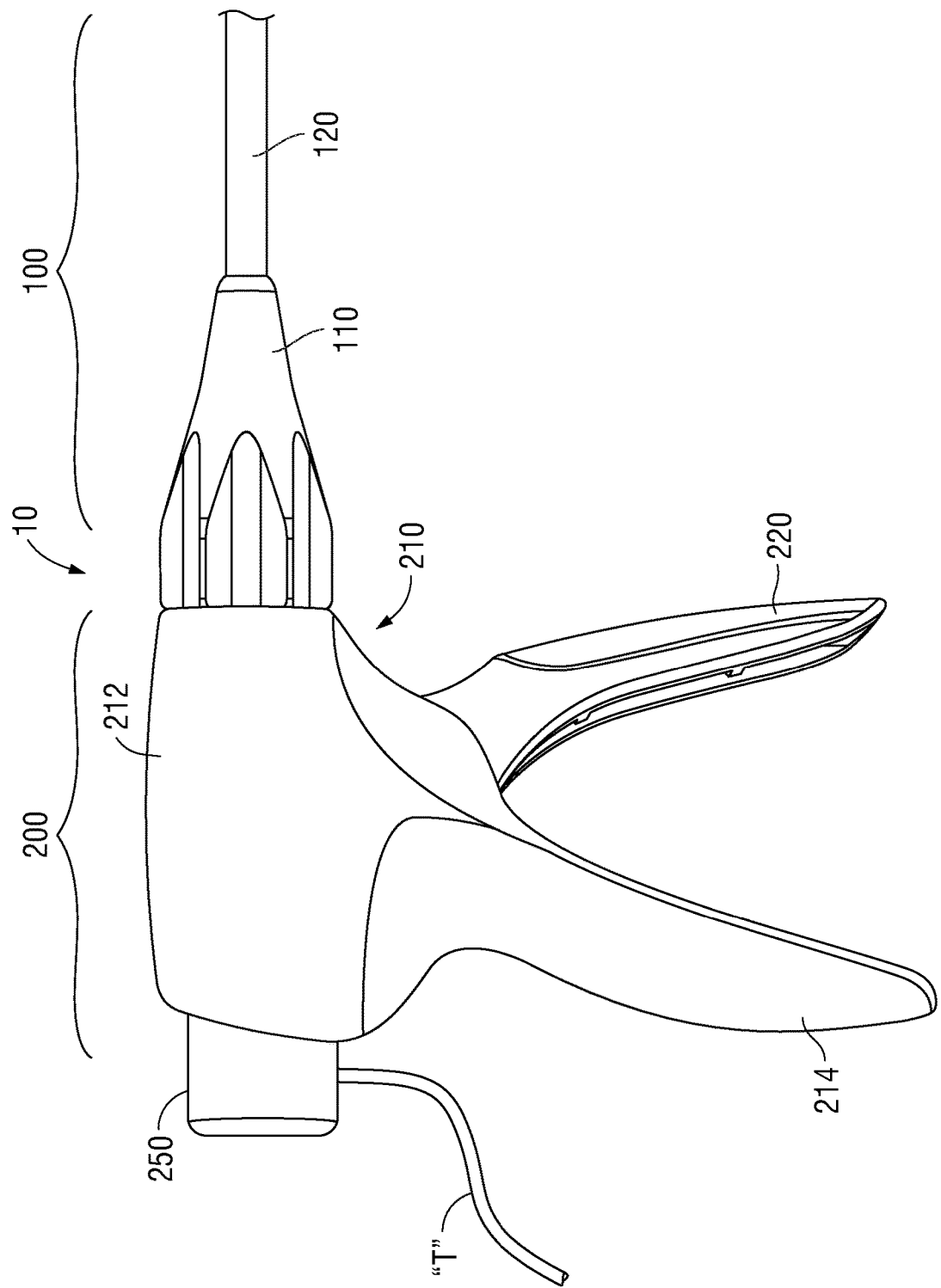
FIG. 1 is a perspective view of a proximal portion of a tissue resecting instrument provided in accordance with the present disclosure.

Referring generally to FIG. 1, a tissue resecting instrument 10 provided in accordance with the present disclosure configured for manual actuation to resect and remove tissue includes an end effector assembly 100 and a handpiece assembly 200. Tissue resecting instrument 10 may be adapted to connect to a fluid collection reservoir (not shown) via outflow tubing "T" for collecting fluid suctioned through tissue resecting instrument 10 during use or, alternatively, may be configured to internally retain the fluid suctioned therethrough, e.g., via internal outflow tubing and an internal fluid collection reservoir (not shown). As an alternative to manual actuation, tissue resecting instrument 10 may incorporate or couple to a powered drive source (not shown), e.g., a motor, for powered actuation thereof.

With continued reference to FIG. 1, tissue resecting instrument 10 may be configured as a single-use instrument that is discarded after use or sent to a manufacturer for reprocessing, a reusable instrument capable of being cleaned and/or sterilized for repeated use by the end-user, or a partially-single-use, partially-reusable instrument. With respect to partially-single-use, partially-reusable configurations, handpiece assembly 200 may be configured as a cleanable/sterilizable, reusable component, while end effector assembly 100 is configured as a single-use, disposable/reprocessable component, or vice versa. In any of the above configurations, end effector assembly 100 may be configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies, e.g., end effector assembly 100 (FIGS. 2A and 2B) or end effector assembly 1100 (FIGS. 3A and 3B), with handpiece assembly 200. In other embodiments, end effector assembly 100 is permanently secured to handpiece assembly 200.

Figure 2A:
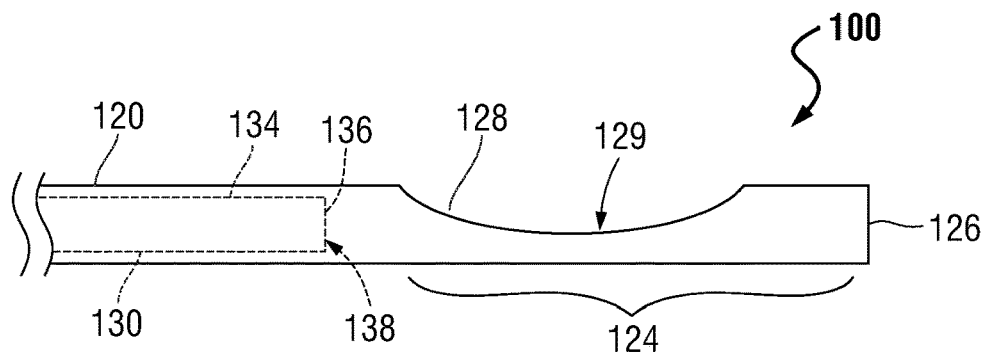
FIGS. 2A and 2B are side views of a distal portion of an end effector assembly of the tissue resecting instrument of FIG. 1 with an inner cutting shaft of the end effector assembly disposed in more-proximal and more-distal positions, respectively.
Figure 2B:
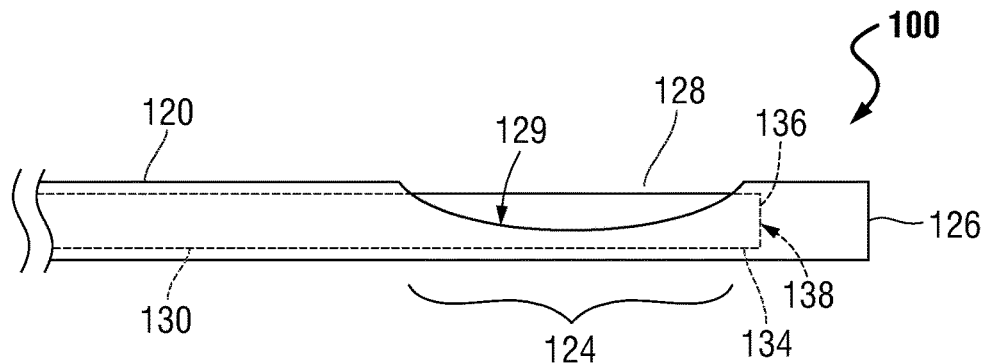
Figure 4:
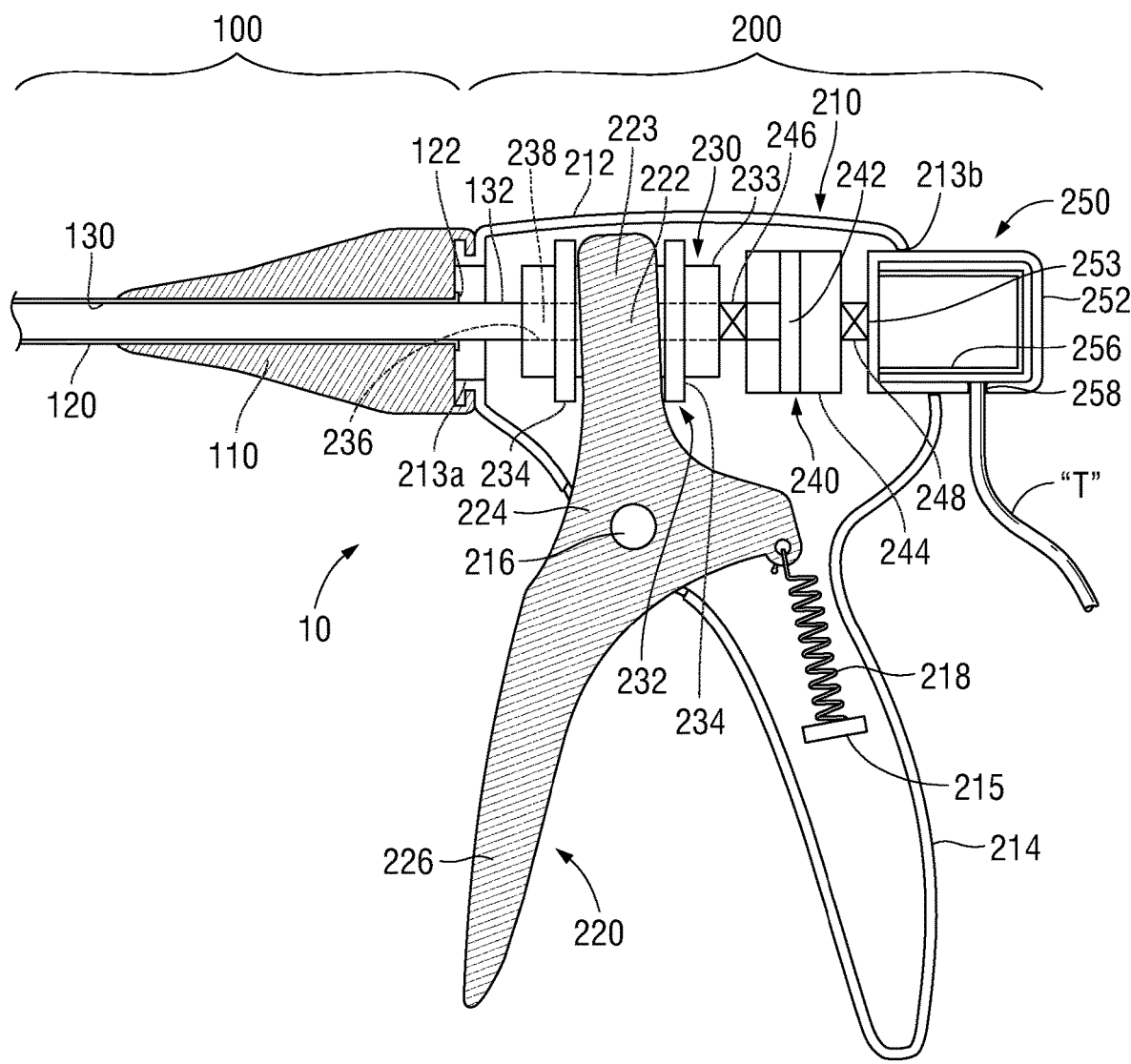
FIG. 4 is a longitudinal, cross-sectional view of the proximal portion of the tissue resecting instrument of FIG. 1.

Referring to FIGS. 2A, 2B, and 4, end effector assembly 100 includes a proximal hub housing 110 which may be formed as a rotation knob configured to rotatably engage handpiece assembly 200 (or may be configured to fixedly engage handpiece assembly 200), an outer shaft 120 fixedly engaged with and extending distally from proximal hub housing 110, an inner cutting shaft 130 movable disposed within outer shaft 120, and an inner drive hub 140 coupled to inner cutting shaft 130 such that movement imparted to inner drive hub 140, e.g., via handpiece assembly 200, as detailed below, drives translation and, in embodiments, translation and/or rotation, of inner cutting shaft 130 within and relative to outer shaft 120.

Outer shaft 120 of end effector assembly 100, includes a proximal end portion 122 fixedly engaged with proximal hub housing 110. Outer shaft 120 further includes a distal end portion 124 defining a closed distal end 126 and a window 128 proximally-spaced from closed distal end 126. Window 128 provides access to the interior of outer shaft 120 and may be surrounded by a cutting edge 129 about the outer perimeter of window 128 so as to facilitate cutting of tissue passing through window 128 and into outer shaft 120.

Inner cutting shaft 130 defines a proximal end portion 132 and a distal end portion 134 defining an open distal end 136. Inner cutting shaft 130 defines an annular cutting edge 138 surrounding open distal end 136 so as to facilitate cutting of tissue passing into inner cutting shaft 130 via open distal end 136. Inner cutting shaft 130 is translatable and, in embodiments, translatable and/or rotatable, within and relative to outer shaft 120. More specifically, inner cutting shaft 130 is configured to translate distally and proximally in a reciprocating motion such that annular cutting edge 138 is exposed within window 128 of outer shaft 120 during at least a portion of the reciprocation motion of inner cutting shaft 130 to enable cutting of tissue extending through window 128. As detailed below, suction is provided to facilitate drawing tissue into window 128 and, thus, cutting and removal of tissue through inner cutting shaft 130. Inner drive hub 140 is engaged about proximal end portion 132 of inner cutting shaft 130.

Figure 3A:
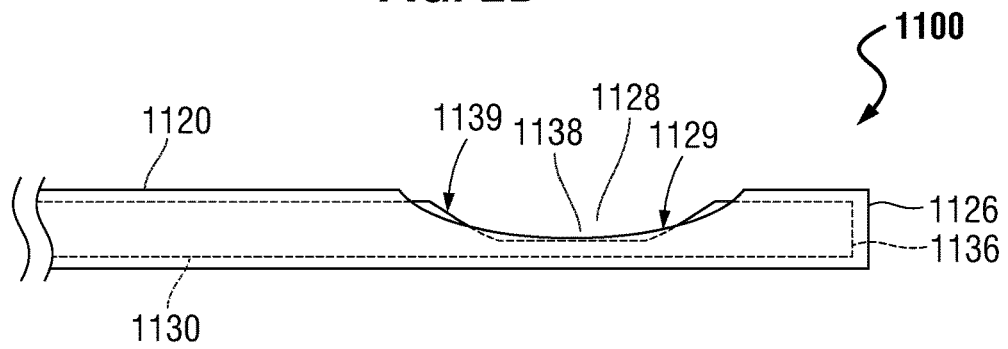
FIGS. 3A and 3B are side views of a distal portion of another end effector assembly configured for use with the tissue resecting instrument of FIG. 1 with an inner cutting shaft of the end effector assembly disposed in first and second rotational positions, respectively.
Figure 3B:
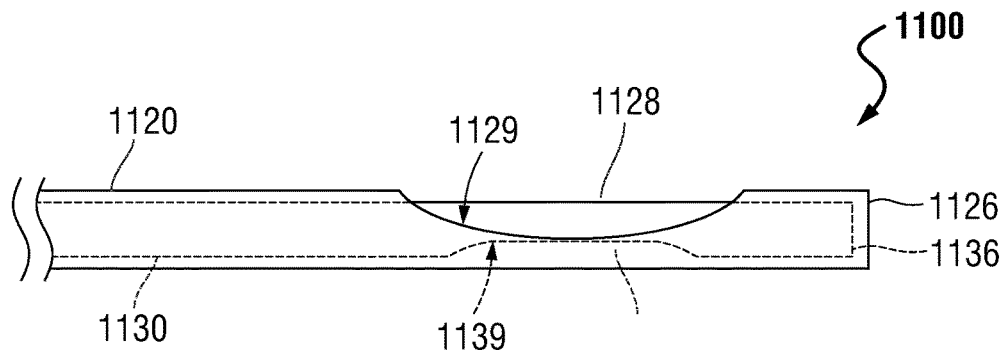

With momentary reference to FIGS. 3A and 3B, another embodiment of an end effector assembly 1100 configured for use with tissue resecting instrument 10 (FIG. 1) is shown. End effector assembly 1100 is similar to and may include any of the features of end effector assembly 100 (FIGS. 2A-2B), except that, rather than providing reciprocation (and, in embodiments, rotation), inner cutting shaft 1130 of end effector assembly 1100 is longitudinally fixed and rotatable relative to outer shaft 1120. End effector assembly 1100 further differs from end effector assembly 100 (FIG. 2A) in that outer shaft 1120 and inner cutting shaft 1130 both define window 1128, 1138 proximally-spaced from the respective distal end 1126, 1136 thereof. Window 1128 and/or window 1138 may be surrounded by a cutting edge 1129, 1139, respectively, configured to facilitate cutting of tissue passing through windows 1128, 1138 upon relative rotation between windows 1128, 1138, e.g., as a result of rotation of inner cutting shaft 1130 relative to outer shaft 1120. Other suitable end effector assemblies including various different outer shaft and inner cutting shaft configurations are also contemplated.

Referring to FIGS. 1 and 4, handpiece assembly 200 generally includes a handle housing 210, a trigger 220 pivotably coupled to handle housing 210, a drive assembly 230 disposed within handle housing 210 and operably coupled to trigger 220, a vacuum generator 240 disposed within handle housing 210 and operably coupled to drive assembly 230, and a tissue collection cartridge 250 releasably coupled to handle housing 210 (although in other embodiments tissue collection cartridge is permanently coupled to handle housing 210) and operably coupled to vacuum generator 240. Outflow tubing "T" couples tissue collection cartridge 250 to the fluid collection reservoir (not shown) for collecting fluid suctioned through tissue resecting instrument 10 during use. Alternatively, as noted above, handle housing 210 may include internal outflow tubing and an internal fluid collection reservoir (not shown) coupled to tissue collection cartridge 250 to retain the fluid suctioned through tissue resecting instrument 10 during use within tissue resecting instrument 10. Further, as also noted above, tissue resecting instrument 10 may be configured for powered actuation and, in such embodiments, a motor and one or more actuation buttons (not shown) replaces trigger 220. Other suitable powered or manual actuators are also contemplated.

Handle housing 210 defines a pistol-grip configuration, although other configurations are also contemplated, and includes a barrel portion 212 and a fixed handle portion 214 depending from barrel portion 212. Barrel portion 212 includes a distal port 213a about which proximal hub housing 110 of end effector assembly 100 is configured to releasably engage handle housing 210, e.g., via snap-fit engagement, with inner cutting shaft 130 and inner drive hub 140 extending through distal port 213a into handle housing 210. Barrel portion 212 also includes a proximal port 213b configured to receive (releasably or permanently) at least a portion of tissue collection cartridge 250, e.g., in threaded engagement, friction-fit engagement, etc. Barrel portion 212 of handle housing 210 houses drive assembly 230 and vacuum generator 240 therein.

Handle housing 210 supports a pivot 216 therein about which trigger 220 is pivotably coupled, thereby enabling trigger 220 to pivot relative to fixed handle portion 214 of handle housing 210 through an actuation stroke between an un-actuated position, wherein trigger 220 is further-spaced from fixed handle portion 214, and an actuated position, wherein trigger 220 is closer to fixed handle portion 214. The actuation stroke of trigger 220 includes a forward stroke portion involving movement of trigger 220 from the un-actuated position to the actuated position, and a return stroke portion, involving movement of trigger 220 from the actuated position back to the un-actuated position. Fixed handle portion 214 includes an internal support 215 retaining a first end of a biasing member 218, e.g., an extension spring, in fixed position relative to fixed handle portion 214. A second end of biasing member 218 is engaged with trigger 220 such that biasing member 218 biases trigger 220 towards the un-actuated position.

Trigger 220 includes an upper drive portion 222, an intermediate pivot portion 224, and a lower manipulation portion 226, and may be formed as a single, monolithic piece or may otherwise be formed as a unitary structure. Intermediate pivot portion 224 of trigger 220 is pivotably coupled to handle housing 210 about pivot 216. Upper drive portion 222 of trigger 220 extends upwardly from intermediate pivot portion 224 into handle housing 210 to operably couple to drive assembly 230. More specifically, upper drive portion 222 defines a bifurcated configuration including a pair of spaced-apart upper drive flanges 223 disposed on either side of drive assembly 230 and operably coupled thereto. Lower manipulation portion 226 of trigger 220 extends downwardly from intermediate pivot portion 224 exteriorly from handle housing 210 to enable manual manipulation thereof by a user between the un-actuated and actuated positions.

Drive assembly 230 of handpiece assembly 200 includes a mandrel 232 engaged about an inner shaft 236 defining a lumen 238 extending therethrough. Mandrel 232 includes a body 233 and pair of longitudinally-spaced rims 234 disposed on body 233 and is configured to receive upper drive flanges 223 of upper drive portion 222 of trigger 220 longitudinally between rims 234 on either side of body 233. In this manner, pivoting of trigger 220 towards the actuated position urges upper drive flanges 223 into the distal rim of the pair of longitudinally-spaced rims 234 to thereby urge mandrel 232 distally through handle housing 210. On the other hand, pivoting of trigger 220 towards the un-actuated position urges drive flanges 223 into the proximal rim of the pair of longitudinally-spaced rims 234 to thereby urge mandrel 232 proximally through handle housing 210.

Inner drive hub 140 of end effector assembly 100 is configured to releasably engage mandrel 232, e.g., via mechanical fastening, friction-fit engagement, magnetic coupling, etc., upon engagement of end effector assembly 100 with handpiece assembly 200 such that inner drive hub 140 is fixed relative to mandrel 232, and such that the interior of inner cutting shaft 130 of end effector assembly 100 is disposed in fluid communication with lumen 238 of inner shaft 236. Of course, in embodiments where end effector assembly 100 is permanently secured to handpiece assembly 200, inner drive hub 140 of end effector assembly 100 is permanently engaged to mandrel 232.

With inner drive hub 140 fixed relative to mandrel 232, translation of mandrel 232, e.g., in response to pivoting of trigger 220, likewise translates inner cutting shaft 130 through and relative to outer shaft 120. More specifically, pivoting of trigger 220 relative to handle housing 210 between the un-actuated position and the actuated position translates inner cutting shaft 130 through and relative to outer shaft 120 between a more-proximal position (FIG. 2A) and a more-distal position (FIG. 2B).

With momentary additional reference to FIGS. 3A and 3B, in embodiments where the end effector assembly, e.g., end effector assembly 1100, includes an inner cutting shaft 1130 configured to rotate relative to the outer shaft 1120, rather than inner drive hub 140 being fixed relative to mandrel 232, mandrel 232 may include a coupler (not shown) that is operably engaged within a helical channel (not shown) defined on or otherwise associated with inner drive hub 140. As a result of such a configuration, longitudinal translation of mandrel 232, e.g., in response to actuation of trigger 220, effects rotation of inner drive hub 140 and, thus, inner cutting shaft 1130.

In embodiments where the end effector assembly, e.g., end effector assembly 1100, includes an inner cutting shaft 1130 configured to both reciprocate and rotate relative to the outer shaft 1120, rather than inner drive hub 140 being fixed relative to mandrel 232, mandrel 232 or inner drive hub 140 may include a helical channel (not shown) defined thereon or otherwise associated therewith and a coupler (not shown) may be fixed within handle housing 210 and engaged within the helical channel. As a result of such a configuration, longitudinal translation of mandrel 232, e.g., in response to actuation of trigger 220, effects both rotation and translation of inner drive hub 140 and, thus, inner cutting shaft 1130.

Referring again to FIGS. 1 and 4, vacuum generator 240 is disposed within handle housing 210 and operably coupled to drive assembly 230. Vacuum generator 240 includes a chamber 244 that is disposed in fluid communication with lumen 238 of inner shaft 236 of drive assembly 230 which, as noted above, is disposed in fluid communication with the interior of inner cutting shaft 130 of end effector assembly 100. As a result, vacuum generated by vacuum generator 240 suctions tissue and fluid through window 128 of outer shaft 120, open distal end 136 of inner cutting shaft 130, lumen 238 of inner shaft 236 of drive assembly 230, and into chamber 244 of vacuum generator 240.

Vacuum generator 240, more specifically, includes a plunger 242 sealingly engaged and slidably disposed within chamber 244. In embodiments, inner shaft 236 defines the push-rod of plunger 242, although other configurations are also contemplated. Plunger 242 is coupled with mandrel 232, e.g., via inner shaft 236 or in any other suitable manner, such that as mandrel 232 is translated through handle housing 210, plunger 242 is similarly translated through chamber 244. More specifically, when mandrel 232 is translated distally, e.g., in response to movement of trigger 220 from the un-actuated position towards the actuated position to move inner cutting shaft 130 from the more-proximal position (FIG. 2A) towards the more-distal position (FIG. 2B), plunger 242 is moved distally through chamber 244 to increase the volume of chamber 244 and generate vacuum within chamber 244, thereby establishing suction through lumen 238 of inner shaft 236 and inner cutting shaft 130. In this manner, as inner cutting shaft 130 is moved from the more-proximal position (FIG. 2A) towards the more-distal position (FIG. 2B), tissue and fluid are suctioned through window 128 of outer shaft 120, tissue is cut by open distal end 136 of inner cutting shaft 130, and the cut tissue and fluid are suctioned proximally through lumen 238 of inner shaft 236 of drive assembly 230 and into chamber 244 of vacuum generator 240.

When mandrel 232 is returned proximally, e.g., in response to movement of trigger 220 from the actuated position back towards the un-actuated position to move inner cutting shaft 130 from the more-distal position (FIG. 2B) back towards the more-proximal position (FIG. 2A), plunger 242 is moved proximally through chamber 244 to push tissue and fluid, under pressure, from chamber 244 of vacuum generator 240 into tissue collection cartridge 250. One-way valves 246, 248 are disposed between vacuum generator 240 and drive assembly 230 and between vacuum generator 240 and tissue collection cartridge 250, respectively, to inhibit pumping tissue and fluid distally from vacuum generator 240 into lumen 238 of inner shaft 236 and drawing tissue and fluid distally from tissue collection cartridge 250 back into vacuum generator 240, respectively.

Tissue collection cartridge 250, as noted above, is releasably coupled to handle housing 210. Tissue collection cartridge 250, more specifically, may be configured to releasably engage proximal port 213b of handle housing 210 via threaded engagement or other suitable engagement. Tissue collection cartridge 250 includes an outer housing 252 defining a distal port 253 configured to couple, in fluid communication, with chamber 244 of vacuum generator 240 upon engagement of tissue collection cartridge 250 with handle housing 210. In this manner, tissue and fluid suctioned through window 128 of outer shaft 120, open distal end 136 of inner cutting shaft 130, lumen 238 of inner shaft 236 of drive assembly 230, and into chamber 244 of vacuum generator 240, may then be urged into tissue collection cartridge 250. One-way valve 248, as an alternative to being part of vacuum generator 240, may be disposed within distal port 253 of tissue collection cartridge 250.

Tissue collection cartridge 250 further includes an internal filter 256 disposed within outer housing 252 that is configured to permit passage of fluid therethrough but inhibit the passage of tissue therethrough. An outflow port 258 configured to enable connection of outflow tubing "T" with tissue collection cartridge 250 enables the fluid that passes through filter 256 to drain out from tissue collection cartridge 250 to a fluid collection reservoir (not shown).

Referring generally to FIGS. 1-2B and 4, in preparation for use, if not already done so, end effector assembly 100 is engaged with handpiece assembly 200, tissue collection cartridge 250 is engaged with handle housing 210 of handpiece assembly 200, and outflow tubing "T" is coupled between tissue collection cartridge 250 and the fluid collection reservoir (not shown). In embodiments, any or all of the above engagements and/or couplings are accomplished during manufacturing and, thus, need not be performed by the end-user.

With tissue resecting instrument 10 assembled as detailed above, in use, tissue resecting instrument 10 is inserted into an internal body cavity or organ, e.g., a uterus, such that the distal end portion of end effector assembly 100 is positioned adjacent tissue to be removed. Tissue resecting instrument 10 may be inserted through an endoscope, e.g., a hysteroscope, or other instrument, or may be used independently. Once tissue resecting instrument 10 is positioned as desired adjacent tissue to be removed, tissue resecting instrument 10 is activated by pivoting trigger 220 relative to fixed handle portion 214 of handle housing 210 through the actuation stroke from the un-actuated position to the actuated position and back to the un-actuated position to thereby reciprocate inner cutting shaft 130 through and relative to outer shaft 120 (e.g., from the more-proximal position (FIG. 2A) to the more-distal position (FIG. 2B) and back to the more-proximal position (FIG. 2A)), suction cut tissue and fluid through inner cutting shaft 130 and lumen 238 of inner shaft 236 into vacuum generator 240, and urge tissue and fluid from vacuum generator 240 into tissue collection cartridge 250. Tissue resecting instrument 10 may be repeatedly actuated as detailed above to cut and remove target tissue as desired. The tissue urged into tissue collection cartridge 250 during use is retained therein, while the fluid urged into tissue collection cartridge 250 passes through filter 256, outflow port 258, and outflow tubing "T" to the fluid collection reservoir (not shown).

Once the desired tissue is removed, tissue resecting instrument 10 may be removed from the surgical site. Thereafter, end effector assembly 100 and tissue collection cartridge 250 may be disengaged from handpiece assembly 200. End effector assembly 100 and/or handpiece assembly 200 may then be discarded, sent for reprocessing, or sterilized for reuse. Tissue collection cartridge 250 may be sent to pathology for analyzing the tissue retained therein or may likewise be discarded.

Turning to FIGS. 5A-8, various embodiments of tissue collection cartridges 350, 450, 550, 650 similar to tissue collection cartridge 250 (FIGS. 1 and 4) and configured for use with tissue resecting instrument 10 (FIG. 1) or another suitable surgical instrument are provided in accordance with the present disclosure. Tissue collection cartridges 350, 450, 550, 650 may each include the features of tissue collection cartridge 250 (FIGS. 1 and 4) except as explicitly contradicted below. Further, to the extent consistent, any of the features of any one tissue collection cartridge 350, 450, 550, 650 may be used in conjunction with the features of any other tissue collection cartridge 350, 450, 550, 650.

Figure 5A:
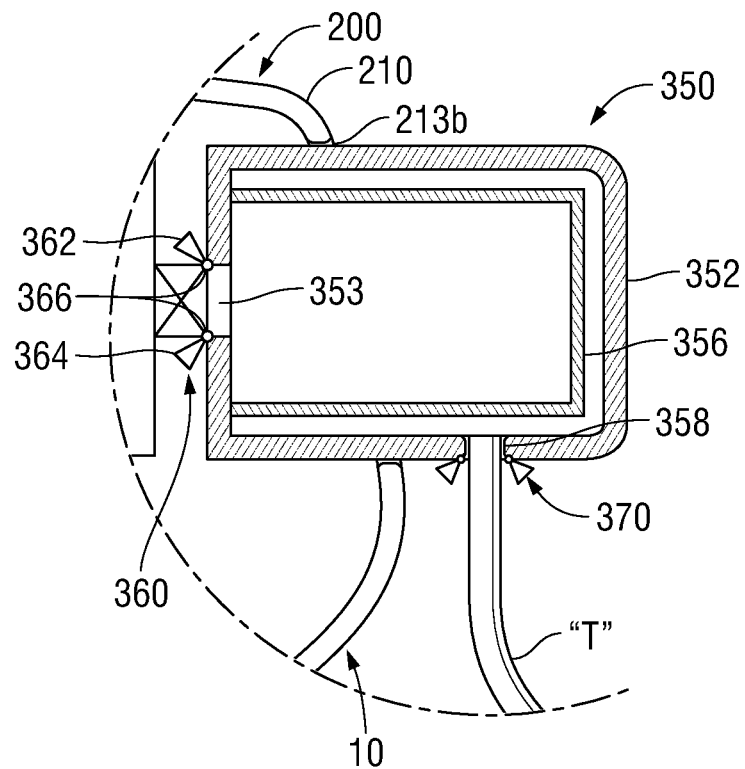
FIG. 5A is a longitudinal, cross-sectional view of a tissue collection cartridge provided in accordance with the present disclosed shown engaged with the tissue resecting instrument of FIG. 1.
Figure 5B:
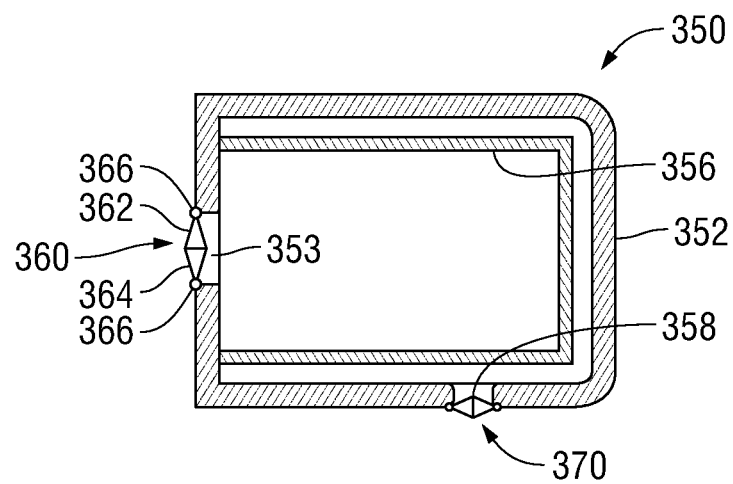
FIG. 5B is a longitudinal, cross-sectional view of the tissue collection cartridge of FIG. 5A after disengagement from the tissue resecting instrument of FIG. 1.

With reference to FIGS. 5A and 5B, tissue collection cartridge 350 includes an outer housing 352 defining a distal port 353, an internal filter 356 disposed within outer housing 352, and an outflow port 358 defined through outer housing 352 to enable connection of outflow tubing "T" with tissue collection cartridge 350. Tissue collection cartridge 350 further includes a first latch 360 operably associated with distal port 353. First latch 360 includes first and second latch arms 362, 364. As illustrated in FIG. 5A, with tissue collection cartridge 350 engaged within proximal port 213b of handle housing 210 of handpiece assembly 200, first and second latch arms 362, 364 are retained in an open condition wherein first and second latch arms 362, 364 are unlatched from one another and allow fluid and tissue to pass into tissue collection cartridge 350. First and second latch arms 362, 364 may be retained in the open condition via interference-engagement with other structures, e.g., vacuum generator 240 of handpiece assembly 200, or may be retained in the open condition in any other suitable manner.

As shown in FIG. 5B, upon disengagement of tissue collection cartridge 350 from handle housing 210, first and second latch arms 362, 364 move under bias to a closed condition wherein first and second latch arms 362, 364 are latched with one another to close distal port 353 of tissue collection cartridge 350. In embodiments, the latched first and second latch arms 362, 364 seal distal port 353 closed. The bias to close first and second latch arms 362, 364 upon disengagement of tissue collection cartridge 350 from handle housing 210 may be provided by living hinges 366 coupling first and second latch arms 362, 364 with handle housing 210, or in any other suitable manner. That is, once the interference-engagement is removed, e.g., upon disengagement of tissue collection cartridge 350 from handle housing 210, first and second latch arms 362, 364 are allowed to move to the closed condition. First latch 360 thus protects tissue collection cartridge 350, inhibits contaminants from entering tissue collection cartridge 350, and inhibits tissue from escaping tissue collection cartridge 350 once tissue collection cartridge 350 is disengaged from handle housing 210. First latch 360, in the closed condition, may be permanently closed (requiring tissue collection cartridge 350 to be broken or accessed in another manner to retrieve the tissue therein), or may be releasable from the closed condition, e.g., using an appropriate tool, a release button, etc.

Tissue collection cartridge 350 may additionally include a second latch 370 similar to first latch 360 except that second latch 370 is configured to close (and, in embodiments, seal) outflow port 358 upon disconnection and removal of outflow tubing "T" therefrom.

Figure 6A:
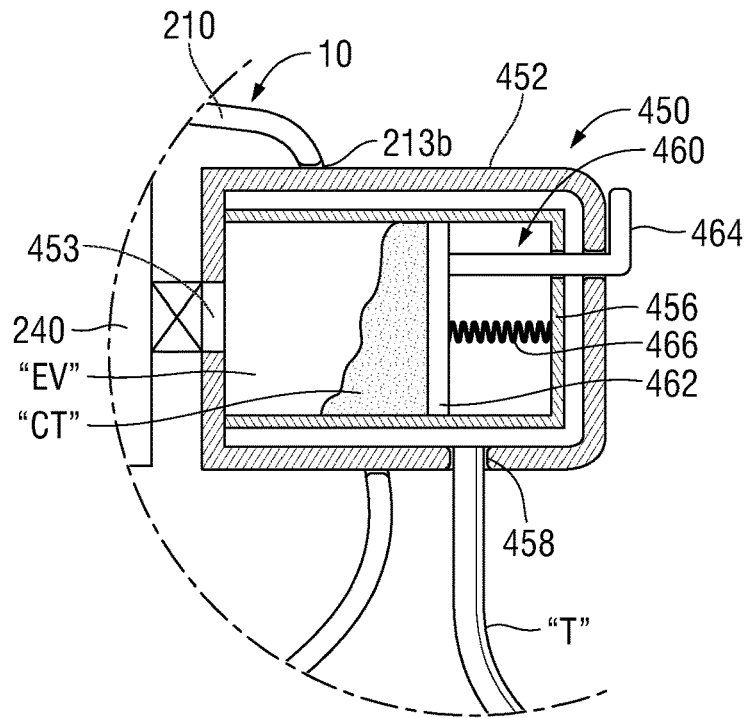
FIG. 6A is a longitudinal, cross-sectional view of another tissue collection cartridge provided in accordance with the present disclosed shown engaged with the tissue resecting instrument of FIG. 1 during use.
Figure 6B:
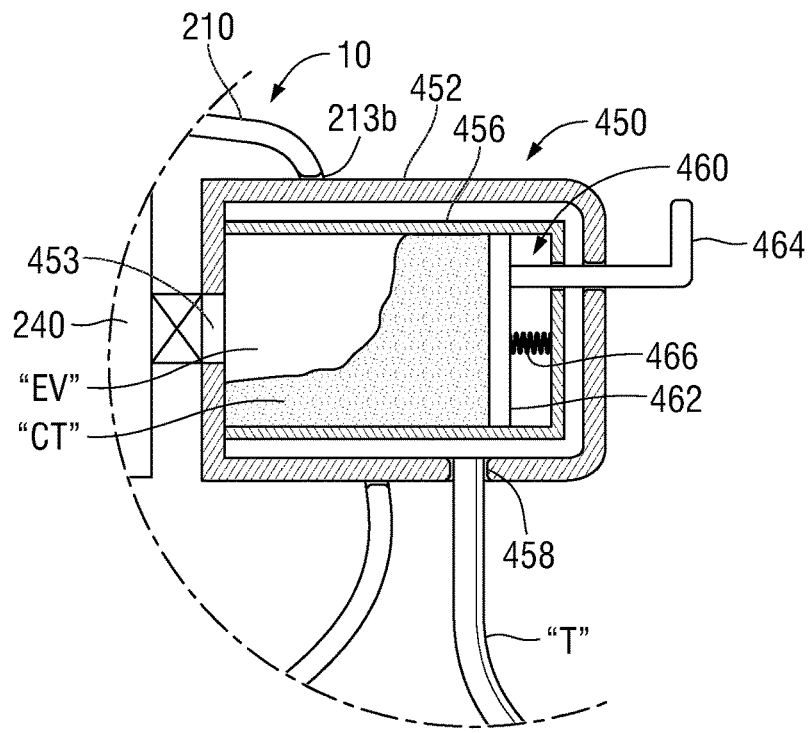
FIG. 6B is a longitudinal, cross-sectional view of the tissue collection cartridge of FIG. 6A shown engaged with the tissue resecting instrument of FIG. 1 after further use.

Referring to FIGS. 6A and 6B, tissue collection cartridge 450 includes an outer housing 452 defining a distal port 453, an internal filter 456 disposed within outer housing 452, and an outflow port 458 defined through outer housing 452 to enable connection of outflow tubing "T" with tissue collection cartridge 450. Tissue collection cartridge 450 further includes a mechanical fill indicator 460. Mechanical fill indicator 460 includes a movable wall 462 slidably disposed within outer housing 452, an indicator flag 464 engaged with movable wall 462 and extending therefrom exteriorly of outer housing 452, and a spring 466, e.g., a compression spring, coupled between movable wall 462 and outer housing 452 to bias movable wall 462 towards a first position (FIG. 6A).

As shown in FIG. 6A, in the first position of movable wall 462, movable wall 462 is positioned such that the effective volume "EV" of tissue collection cartridge 450 is relatively small. In this position, indicator flag 464 does not protrude or minimally protrudes from outer housing 452.

As shown in FIG. 6B, as tissue resecting instrument 10 is used and cut tissue "CT" is collected within tissue collection cartridge 450, the cut tissue "CT" starts to fill the effective volume "EV" and, eventually, urges movable wall 462 against the bias of spring 466 to increase the effective volume "EV" of tissue collection cartridge 450 to accommodate more cut tissue "CT." As movable wall 462 is moved against the bias of spring 466, indicator flag 464 is moved to protrude or protrude further from outer housing 452. In this manner, the position of indicator flag 464 provides the user with an indication of the fill level of tissue collection cartridge 450. Thus, the user is notified to remove tissue collection cartridge 450 and replace it with a new tissue collection cartridge 450, to switch devices, or to end the procedure before an overfill condition occurs.

Figure 7:
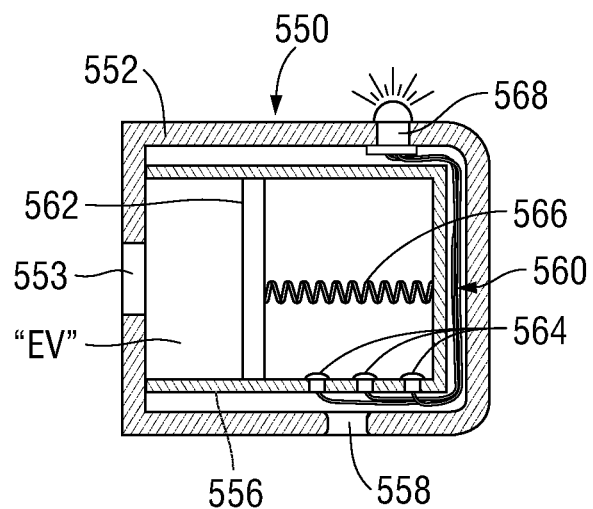
FIG. 7 is a longitudinal, cross-sectional view of yet another tissue collection cartridge provided in accordance with the present disclosed and configured for use with the tissue resecting instrument of FIG. 1.

FIG. 7 illustrates a tissue collection cartridge 550 that includes an outer housing 552 defining a distal port 553, an internal filter 556 disposed within outer housing 552, and an outflow port 558 defined through outer housing 552 to enable connection of outflow tubing "T" with tissue collection cartridge 550. Tissue collection cartridge 550 further includes an electromechanical fill indicator 560. Electromechanical fill indicator 560 includes a movable wall 562 slidably disposed within outer housing 552, a plurality of switches 564 disposed within outer housing 552, a spring 566, e.g., a compression spring, coupled between movable wall 562 and outer housing 552, and an indicator device 568, e.g., an LED, speaker, or outer sensory output device.

As tissue resecting instrument 10 (FIG. 1) is used and tissue "CT" (FIGS. 6A & 6B) is collected within tissue collection cartridge 550, similarly as detailed above with respect to tissue collection cartridge 450 (FIGS. 6A & 6B), the collected tissue "CT" (FIGS. 6A & 6B) starts to fill the effective volume "EV" and, eventually, urges movable wall 562 against the bias of spring 566 to increase the effective volume "EV" of tissue collection cartridge 550 to accommodate more collected tissue "CT" (FIGS. 6A & 6B).

As movable wall 562 is moved against the bias of spring 566, movable wall 562 sequentially activates the plurality of switches 564. Upon activation of each switch 564, a signal is provided to indicator device 568 to provide a suitable output, e.g., a blinking light, audible tone, etc., indicating to the user that tissue collection cartridge 550 is starting to fill. Switches 564 may be positioned at any suitable positions and/or intervals to provide any desired indicators, e.g., at 50% full, 75% full, and 90% full. The output of the indicator device 568 may be different for each switch 564, e.g., increasing in intensity as subsequent switches 564 are activated. Similarly as with mechanical fill indicator 460 of tissue collection cartridge 450 (FIGS. 6A & 6B), electromechanical fill indicator 560 of tissue collection cartridge 550 notifies a user as to a relatively fill level of tissue collection cartridge 550 such that the user may remove tissue collection cartridge 550 and replace it with a new tissue collection cartridge 550, switch devices, or end the procedure before an overfill condition occurs.

Figure 8:
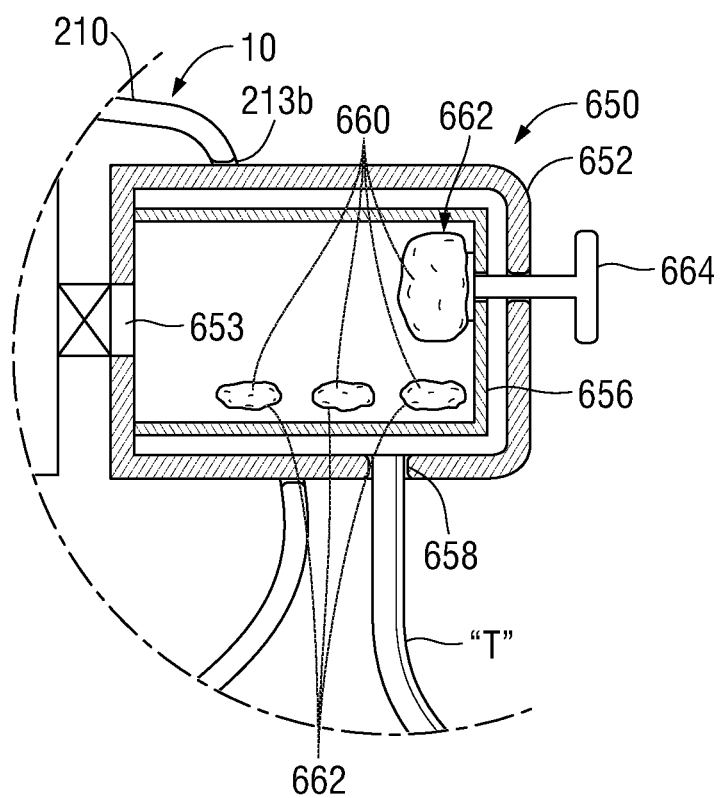
FIG. 8 is a longitudinal, cross-sectional view of still another tissue collection cartridge provided in accordance with the present disclosed shown engaged with the tissue resecting instrument of FIG. 1.

Turning to FIG. 8, tissue collection cartridge 650 includes an outer housing 652 defining a distal port 653, an internal filter 656 disposed within outer housing 652, and an outflow port 658 defined through outer housing 652 to enable connection of outflow tubing "T" with tissue collection cartridge 650. Tissue collection cartridge 650 further includes one or more histological agents 660 (defined herein as any solutions or substances that facilitate the preservation and/or histological processing of collected tissue) disposed within outer housing 652. The one or more histological agents 660 may include one or staining agents (e.g., hematoxylin), clearing agents (e.g., xylene), fixing agents (e.g., formalin), dehydration agents (e.g., ethanol), infiltration agents (e.g., paraffin), preservation agents, other reactive agents, and/or any other suitable agents that facilitate preservation and/or histological processing of collected tissue. The one or more histological agents 660 may be encased within a capsule 662, for example, surgical fluid-soluble (e.g., saline-soluble) capsule, time-release capsule, frangible capsule (e.g., capable of being ruptured upon shaking tissue collection cartridge 650), penetrable capsule (e.g., such that an activator plunger 664 may be manually depressed to penetrate the capsule), etc. In this manner, the histological agents(s) 660 may be released to interact with the collected tissue at a desired time or times.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue resecting instrument, comprising:
   a housing;
   an outer shaft extending distally from the housing and defining a window at a distal end portion thereof;
   an inner cutting shaft extending through the outer shaft, the inner cutting shaft at least one of translatable or rotatable relative to the outer shaft to cut tissue extending through the window;
   a drive assembly coupled to the inner cutting shaft and configured to drive the at least one of translation or rotation of the inner cutting shaft;
   a trigger coupled to the drive assembly, wherein manual actuation of the trigger actuates the drive assembly to drive the at least one of translation or rotation of the inner cutting shaft;
   a vacuum generator coupled to the drive assembly and the inner cutting shaft such that, during a first portion of the actuation of the drive assembly, the vacuum generator is configured to generate vacuum to suction cut tissue through the inner cutting shaft and into the vacuum generator; and
   a tissue collection cartridge configured to engage the housing, the tissue collection cartridge defining a port configured to communicate with the vacuum generator such that, during a second portion of the actuation of the drive assembly, the vacuum generator urges cut tissue from the vacuum generator through the port into the tissue collection cartridge,
   wherein the tissue collection cartridge includes a capsule having at least one histological agent disposed within the capsule and the tissue collection cartridge includes an activator plunger configured to selectively penetrate the capsule to release the at least one histological agent.

2. The tissue resecting instrument according to claim 1, wherein the trigger is pivotably coupled to the housing and movable relative thereto between an un-actuated position and an actuated position to drive the drive assembly to translate the inner cutting shaft between a more-proximal position and a more-distal position.

3. The tissue resecting instrument according to claim 2, wherein the first portion of the actuation of the drive assembly corresponds to movement of the trigger from the un-actuated position to the actuated position, and wherein the second portion of the actuation of the drive assembly corresponds to movement of the trigger from the actuated position to the un-actuated position.

4. The tissue resecting instrument according to claim 1, wherein the at least one histological agent includes at least one of: a staining agent, a clearing agent, a fixing agent, a dehydration agent, or an infiltration agent.

5. The tissue resecting instrument according to claim 1, wherein the capsule is one of: a fluid-soluble capsule, a time-release capsule, or a frangible capsule.

6. A tissue resecting instrument, comprising:
   a housing;
   an outer shaft extending distally from the housing and defining a window at a distal end portion of the outer shaft;
   an inner cutting shaft extending through the outer shaft, the inner cutting shaft including a lumen defined through the inner cutting shaft, the inner cutting shaft moveable relative to the outer shaft to cut tissue extending through the window;
   a drive assembly coupled to the inner cutting shaft and configured to move the inner cutting shaft upon activation of the drive assembly;
   a vacuum generator coupled to the drive assembly and the lumen of the inner cutting shaft such that, during a first portion of the actuation of the drive assembly, the vacuum generator is configured to generate vacuum to suction cut tissue through the inner cutting shaft and into the vacuum generator; and
   a tissue collection cartridge operably associated with the vacuum generator such that, during a second portion of the actuation of the drive assembly, the vacuum generator urges cut tissue from the vacuum generator into the tissue collection cartridge,
   wherein the tissue collection cartridge includes a capsule having at least one histological agent disposed within the capsule and the tissue collection cartridge includes an activator plunger configured to selectively penetrate the capsule to release the at least one histological agent.

7. The tissue resecting instrument according to claim 6, wherein a trigger is pivotably coupled to the housing and is movable relative to the housing between an un-actuated position and an actuated position to move the drive assembly to translate the inner cutting shaft between a more-proximal position and a more-distal position.

8. The tissue resecting instrument according to claim 7, wherein the first portion of the actuation of the drive assembly corresponds to movement of the trigger from the un-actuated position to the actuated position, and wherein the second portion of the actuation of the drive assembly corresponds to movement of the trigger from the actuated position to the un-actuated position.

9. The tissue resecting instrument according to claim 6, wherein the at least one histological agent includes at least one of: a staining agent, a clearing agent, a fixing agent, a dehydration agent, or an infiltration agent.

10. The tissue resecting instrument according to claim 6, wherein the capsule is one of: a fluid-soluble capsule, a time-release capsule, or a frangible capsule.

11. The tissue resecting instrument according to claim 7, wherein actuation of the drive assembly at least one of translates or rotates the inner cutting shaft.

12. The tissue resecting instrument according to claim 7, wherein actuation of the trigger moves the drive assembly, which, in turn, at least one of translates or rotates the inner cutting shaft.

\* \* \* \* \*